(12) United States Patent
Mundt

(10) Patent No.: US 11,116,338 B1
(45) Date of Patent: *Sep. 14, 2021

(54) BODY COMPRESSION SLEEPWEAR WITH A LEG OPENING

(71) Applicant: Matthew J. Mundt, Brookfield, WI (US)

(72) Inventor: Matthew J. Mundt, Brookfield, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/142,396

(22) Filed: Jan. 6, 2021

(51) Int. Cl.
*A47G 9/08* (2006.01)

(52) U.S. Cl.
CPC ...................... *A47G 9/08* (2013.01)

(58) Field of Classification Search
CPC .......... A47G 9/08; A47G 9/083; A47G 9/086; A41B 13/06; A41B 13/065
USPC ......................................................... 5/413 R
See application file for complete search history.

(56) References Cited

U.S. PATENT DOCUMENTS

| | | | | |
|---|---|---|---|---|
| 2,469,700 A | * | 5/1949 | Petroceill | A41B 13/06 2/69.5 |
| 2,803,824 A | * | 8/1957 | Parish | A41B 13/00 2/69.5 |
| 4,759,082 A | * | 7/1988 | Mulligan | A41B 13/06 2/69.5 |
| 4,888,828 A | * | 12/1989 | Tatsuno | A47G 9/086 5/413 R |
| 8,622,943 B2 | * | 1/2014 | Ben-Nun | A61H 9/0078 601/152 |
| D728,198 S | * | 5/2015 | Barski | D2/719 |
| 9,408,484 B2 | * | 8/2016 | Schofield | A47G 9/086 |
| 10,463,179 B1 | * | 11/2019 | Mundt | A41B 13/065 |
| 10,842,202 B1 | * | 11/2020 | Mundt | A47G 9/0238 |
| 10,952,554 B2 | * | 3/2021 | Glavin | A47G 9/08 |
| 2005/0120459 A1 | * | 6/2005 | McConnell | G01K 13/20 2/69.5 |
| 2007/0061968 A1 | * | 3/2007 | Fader | A47D 15/008 5/494 |
| 2009/0222968 A1 | * | 9/2009 | Pisano-Ginter | A41B 13/005 2/80 |
| 2010/0299832 A1 | * | 12/2010 | Alford | A47G 9/086 5/413 AM |
| 2010/0319103 A1 | * | 12/2010 | Smith | A41D 10/00 2/114 |
| 2011/0107502 A1 | | 5/2011 | Dalhausser et al. | |

(Continued)

FOREIGN PATENT DOCUMENTS

GB           1536191 A   * 12/1978   ............... A61G 1/01

*Primary Examiner* — Myles A Throop
(74) *Attorney, Agent, or Firm* — Donald J. Ersler

(57) ABSTRACT

Body compression sleepwear with a leg opening preferably includes a body portion, a neck portion and a leg cover. The body portion includes a first body sheet and a second body sheet. The first and second body sheets include a width which is greatest at the top and smallest at a bottom. A top of the leg cover overlaps a bottom of the first body sheet. Outer sides of the first and second body sheets are sewn to each other to form a body opening at a top and a leg opening at a bottom. A portion of a perimeter of the leg cover is sewn to the bottom perimeter of the second body sheet with exception of a top of the leg cover. A bottom of the neck portion is sewn to a top of the first and second body sheets. However, the neck portion could be eliminated.

16 Claims, 10 Drawing Sheets

(56) References Cited

U.S. PATENT DOCUMENTS

| | | | |
|---|---|---|---|
| 2013/0227786 A1* | 9/2013 | Sack | A41B 13/06 |
| | | | 5/494 |
| 2014/0259274 A1* | 9/2014 | Savage | A41B 13/005 |
| | | | 2/80 |
| 2014/0352061 A1* | 12/2014 | Flora | A41D 15/04 |
| | | | 5/413 R |
| 2017/0065843 A1 | 3/2017 | Foster | |
| 2018/0103689 A1* | 4/2018 | DeLisa | A41B 13/06 |
| 2019/0274366 A1* | 9/2019 | Hilton | A41B 13/06 |
| 2020/0359713 A1* | 11/2020 | Bakouros | A47G 9/08 |
| 2021/0059319 A1* | 3/2021 | Karp | A41B 13/065 |

* cited by examiner

BODY COMPRESSION SLEEPWEAR WITH A LEG OPENING

BACKGROUND OF THE INVENTION

1. Field of the Invention

The present invention relates generally to sleeping garments and more specifically to body compression sleepwear with a leg opening, which allows at least one leg to be positioned outside the body compression sleepwear.

2. Discussion of the Prior Art

Weighted blankets are capable of applying compressive forces to a top and bottom of a user's body, but are also very heavy and expensive. The weighted blankets are not really machine washable and may overheat the user during use. There are also fabric bags, which a user may slip into, but do not provide compressive forces to the outside surface of the body. U.S. Pat. No. 8,622,943 to Ben-Nun discloses a compression bag. Patent publication no. 2017/0065843 to Foster discloses a restriction compression weighted therapy suit. Patent publication no. 2011/0107502 to Dalhausser et al. discloses training and recovery clothing and related methods. U.S. Pat. No. 4,888,828 to Tatsuno discloses a sleeping bag device. U.S. Pat. No. 10,463,179 to Mundt discloses body compression sleepwear. However, the Mundt patent does not include a leg opening for allowing at least one leg to be inserted through a bottom of the body compression sleepwear.

Accordingly, there is a clearly felt need in the art for body compression sleepwear with a leg opening, which applies compressive forces to the outside surface of a user's body; replicates being tightly wrapped in a swaddling garment like a baby; is lightweight; promotes restful sleep; promotes a side sleeping position; and allows at least one leg to be positioned outside the body compression sleepwear.

SUMMARY OF THE INVENTION

The present invention provides body compression sleepwear with a leg opening, which applies compressive forces to the outside surface of a user's body. The body compression sleepwear preferably includes a body portion and a neck portion. The body portion includes a first body sheet and a second body sheet. The first and second body sheets include a substantially oval shape, terminated by a straight end. An outer perimeter of the first and second body sheets are sewn to each other with the exception of the straight end to form a body pocket. The neck portion includes a first neck sheet and a second neck sheet. The first and second neck sheets include a rectangular shape and are folded over to form a double wall. Opposing ends of the first and second neck sheets are sewn to each other to form the neck portion and an entrance opening. A bottom of the neck portion is sewn to the straight end. A length of the neck portion is preferably about 15 percent of a length of the body portion. A width of the neck portion is preferably about 60 percent of a width of the body portion. The material of the body portion and the neck portion is preferably fabricated from a combination Polyester and Lycra® fabric for stretch and memory. Lycra® is a brand name for spandex. The size of the compressive sleepwear is smaller than the user to exert compressive force on the outer surface of the body of the user. The user inserts their legs and arms through the neck portion and into the body pocket. A head of a user is retained outside the neck portion. The user may keep their arms inside the body portion or extend a portion of one or two arms outside the neck portion. It is preferable that the user at least partially bend their legs when in the body pocket, similar to a fetal position of a baby.

The body compression sleepwear with a foot opening preferably includes a body portion, the neck portion and a foot flap. The body portion includes a first body sheet and a second body sheet. The first and second body sheets include a slim oval shape, which is truncated on both ends with a straight edge. An outer perimeter of the first and second body sheets are sewn to each other with the exception of a top straight edge to form a body pocket. A bottom corner edge of the first and second body sheets are also not sewn to each other to form a foot opening. The foot flap is sewn to the bottom corner edge of the first body sheet. The bottom corner edge of the second body sheet is inserted into the foot flap, but may be removed to allow a foot to be inserted through the foot opening. A bottom of the neck portion is sewn to the top straight edge. A length of the neck portion is preferably about 10 percent of a length of the body portion. A width of the neck portion is preferably about 70 percent of a width of the body portion. The material of the body portion and the neck portion is preferably fabricated from a combination Polyester and Lycra® fabric for stretch and memory. The size of the body compressive sleepwear with a foot opening is smaller than the user to exert compressive force on the outer surface of the body of the user.

The body compression sleepwear with a leg opening preferably includes a body portion, a neck portion and a leg cover. The body portion preferably includes a first body sheet and a second body sheet. The first and second body sheets include a width which is greatest at the top and smallest at a bottom. A top of the first and second body sheets include a straight edge. A bottom of the first sheet preferably includes a straight edge. A bottom of the second sheet preferably includes a U-shaped portion. A bottom of the first sheet is truncated at a bottom, such that a top of the leg cover overlaps the bottom of the first sheet. Outer sides of the first and second body sheets are sewn to each other, such that a body opening is formed at a top and a leg opening is formed on a bottom thereof. A portion of a perimeter of the leg cover is sewn to the bottom perimeter of the first and second body sheets with exception of a top of the leg cover. A bottom of the neck portion is sewn to the top straight edge. A length of the neck portion is preferably about 10 percent of a length of the body portion. A width of the neck portion is preferably about 75 percent of a width of the body portion. However, the neck portion could be eliminated. Further, the body compression sleepwear with a leg opening could be fabricated from single piece of material. The material of the body portion, the neck portion and the leg cover is preferably a combination Polyester and Lycra® fabric for stretch and memory.

Accordingly, it is an object of the present invention to provide compression sleepwear, which applies compressive forces to the outside surface of a user's body.

It is further object of the present invention to provide body compression sleepwear, which replicates being tightly wrapped in a swaddling garment like a baby.

It is another object of the present invention to provide body compression sleepwear, which is lightweight.

It is yet a further object of the present invention to provide body compression sleepwear, which promotes restful sleep.

It is yet a further object of the present invention to provide body compression sleepwear, which promotes a side sleeping position.

Finally, it is another object of the present invention to provide body compression sleepwear with a leg opening with allows at least one leg to be inserted through a bottom thereof.

These and additional objects, advantages, features and benefits of the present invention will become apparent from the following specification.

DETAILED DESCRIPTION OF THE PREFERRED EMBODIMENTS

Figure 1:
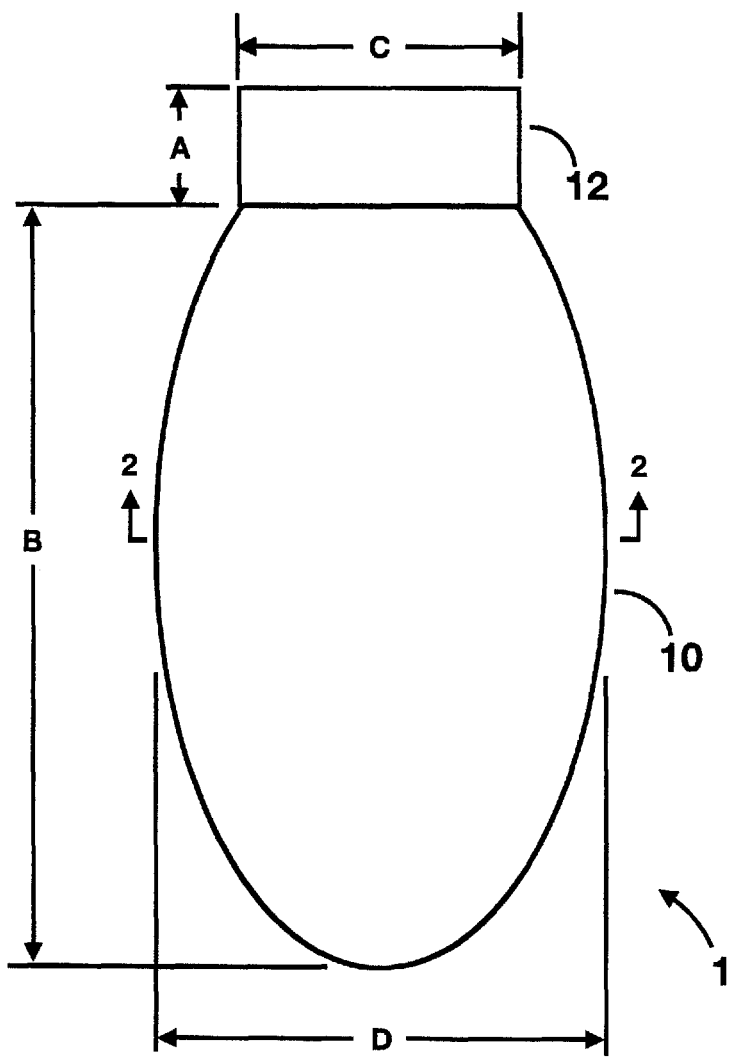
FIG. 1 is a front view of body compression sleepwear in accordance with the present invention.
Figure 2:
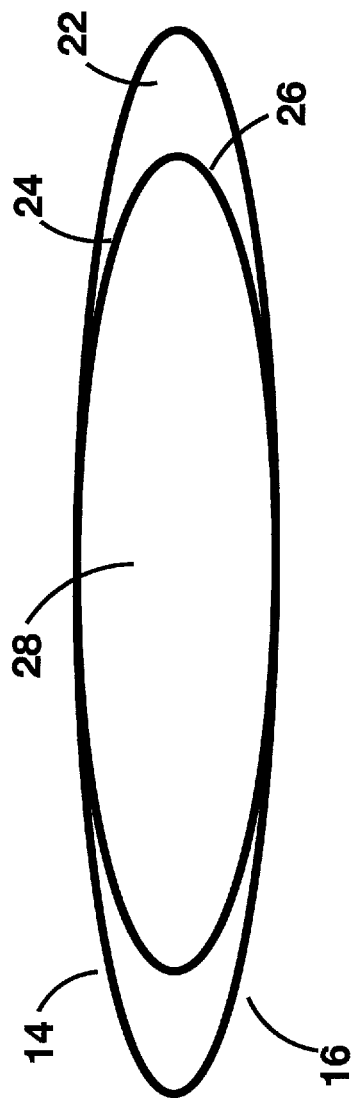
FIG. 2 is a cross sectional view of body compression sleepwear cut through FIG. 1 and a thickness slightly increased for illustration purposes in accordance with the present invention.
Figure 3:
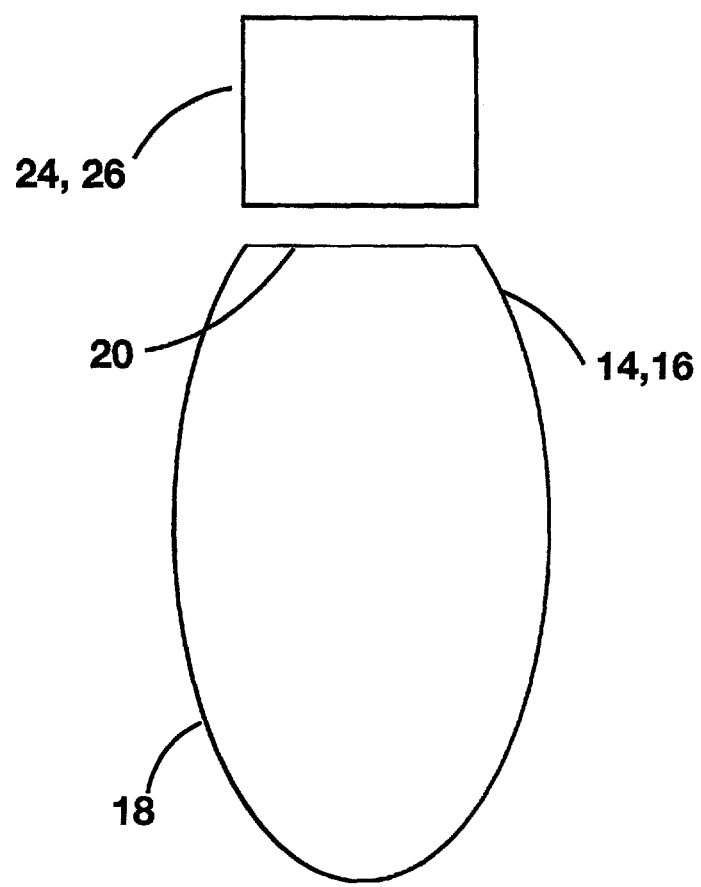
FIG. 3 is a front exploded view of a first or second neck sheet and a first or second body sheet, before sewing of body compression sleepwear in accordance with the present invention.

With reference now to the drawings, and particularly to FIG. 1, there is shown a front view of body compression sleepwear 1. The body compression sleepwear 1 preferably includes a body portion 10 and a neck portion 12. With reference to FIGS. 2-3, the body portion 10 includes a first body sheet 14 and a second body sheet 16. The first and second body sheets 14, 16 include a substantially oval shape 18, terminated by a straight end 20. An outer perimeter of the first and second body sheets 14, 16 are preferably sewn to each other, but could be attached to each other with any suitable process with the exception of the straight end to form a body pocket 22. The first and second body sheets 14, 16 may be fabricated from a single piece material. The neck portion 12 includes a first neck sheet 24 and a second neck sheet 26. The first and second neck sheets 24, 26 include a rectangular shape and are folded over to form a double wall. Opposing ends of the first and second neck sheets 24, 26 are preferably sewn to each other, but could be attached to each other with any suitable process to form the neck portion 12 and an entrance opening 28. The first and second neck sheets 24, 26 may be fabricated from a single piece of material. A bottom of the first neck sheet 14 is preferably sewn to the straight end 20 of the first body sheet 14, but could be attached to the straight end 20 with any suitable process and a bottom of the second neck sheet 16 is preferably sewn to the straight end 20 of the second body sheet 16. The body portion 10 and the neck portion 12 may fabricated from a single piece of material.

Figure 3A:
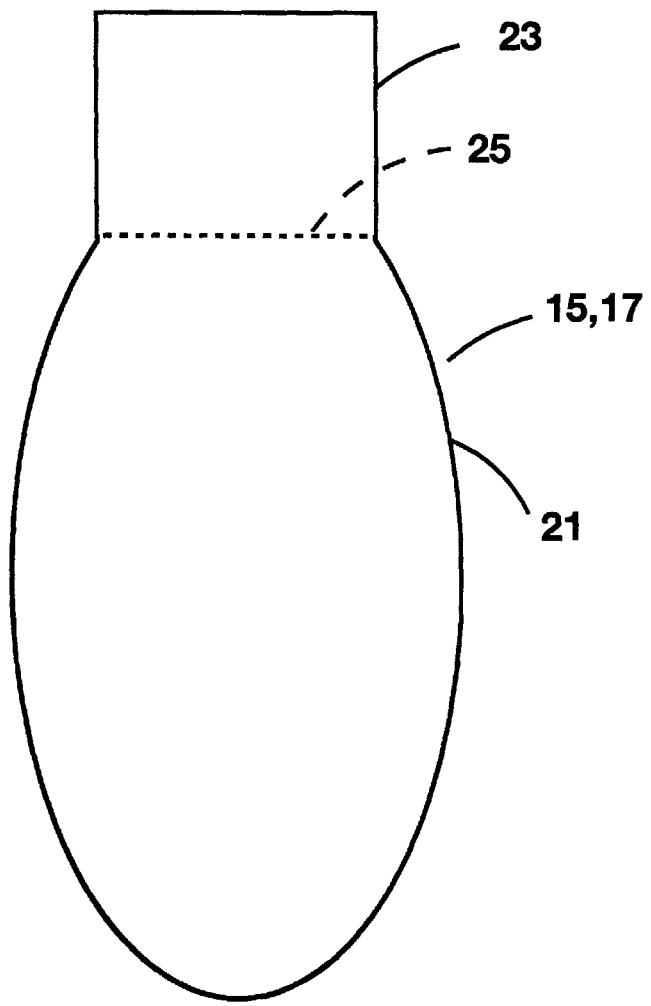
FIG. 3a is a front view of a first body side sheet or a second body side body sheet, before sewing of body compression sleepwear in accordance with the present invention.

With reference to FIG. 3a, a first or second body side sheet 15, 17 is shown. The first or second body side sheet 15, 17 include a body portion 21 and a neck portion 23 that extends from the body portion 21. The neck portion is folded over to line 25 to create a double wall. A perimeter of the first and second body side sheets 15, 17 are preferably sewn to each other, but could be attached to each other with any suitable process. A top of the neck portion 23 of the first and second body sides 15, 17 are sewn or attached to each other to form the entrance opening 28. A length "A" of the neck portion 12 is preferably about 15 percent of a length "B" of the body portion 10. A width "C" of the neck portion 12 is preferably about 60 percent of a width "D" of the body portion 10. The material of the body portion 10 and the neck portion 12 is preferably fabricated from a combination Polyester and Lycra® fabric. The Lycra® fabric has preferred stretch of about 170%. The preferable percentage of Lycra® is about 11% and the preferable percentage of Polyester is about 89%.

The Lycra® fabric has preferred stretch of about 170%. However, other preferable percentages are about Polyester 95% and Lycra® 5%; about Polyester 92% and Lycra® 8%; about Polyester 90% and Lycra® 10%; about Polyester 87% and Lycra® 13%; about Polyester 85% and Lycra® 15%; and about Polyester 82% and Lycra® 18%. The Polyester and Lycra® combination provide a material that is stretchable and has memory to return to its original unstretched length.

Figure 4:
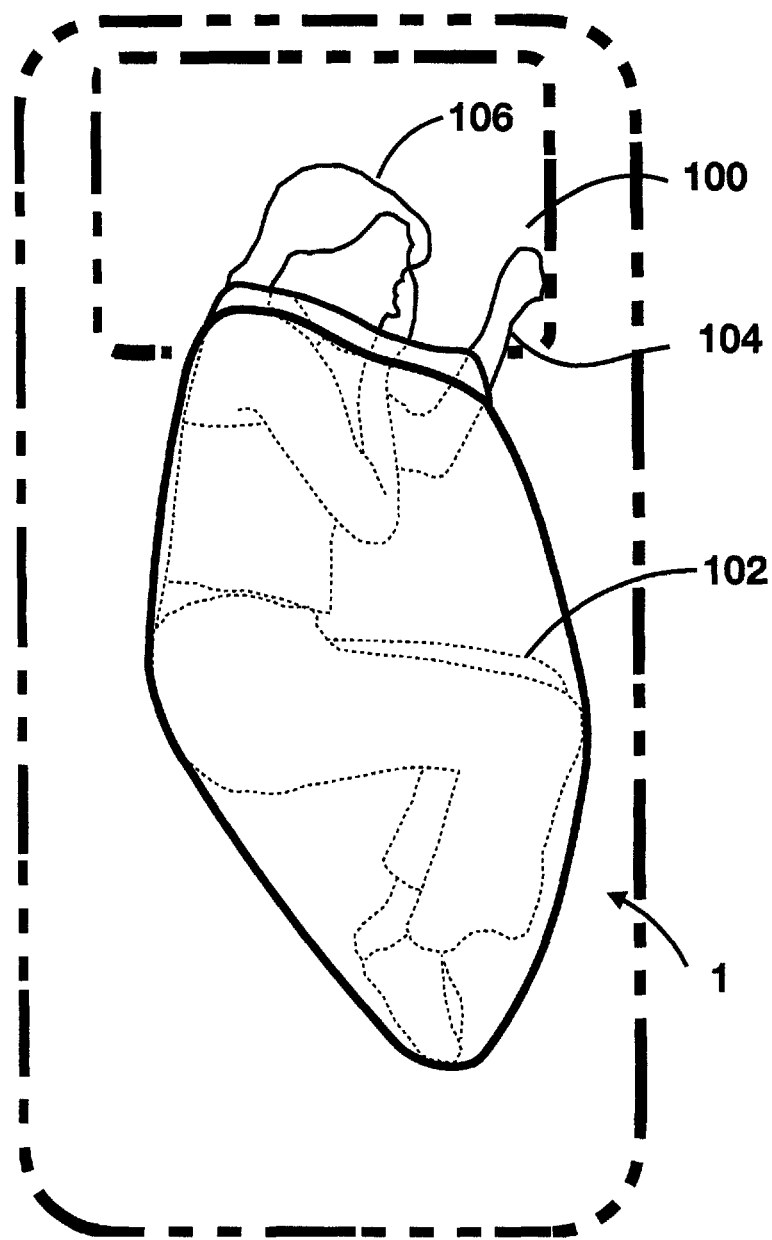
FIG. 4 is a top view of a user contained inside compression sleepwear in accordance with the present invention.

With reference to FIG. 4, a width and length of the body compression sleepwear 1 is smaller than a width and length of a user 100 to exert compressive force on the outer surface of the body of the user 100. The user 100 inserts their legs 102 and arms 104 through the entrance opening 28 and into the body pocket 22. A head 106 of a user 100 is not retained inside the neck portion. The user 100 may keep their arms 104 inside the body cavity 22 or extend a portion of one or two arms 104 outside the neck portion 12. It is preferable that the user 100 at least partially bend their legs 102 when in the body pocket 22, similar to a fetal position of a baby. The body compression sleepwear 1 preferably comes in different sizes for adults, children and babies.

Figure 5:
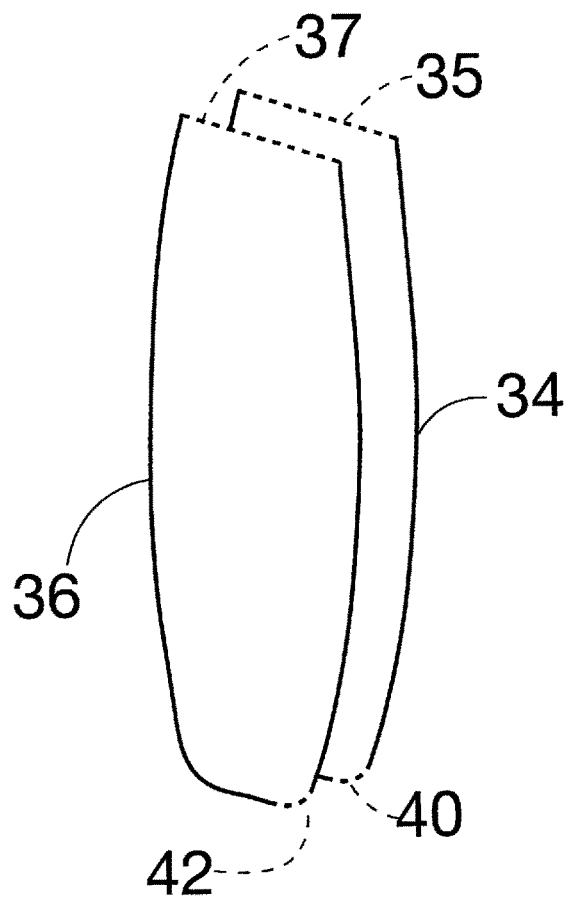
FIG. 5 is an exploded perspective view of first and second body sheets of a body compression sleepwear with a foot opening illustrating where the first and second body sheets are not sewn to create the foot opening and a pocket in accordance with the present invention.
Figure 6:
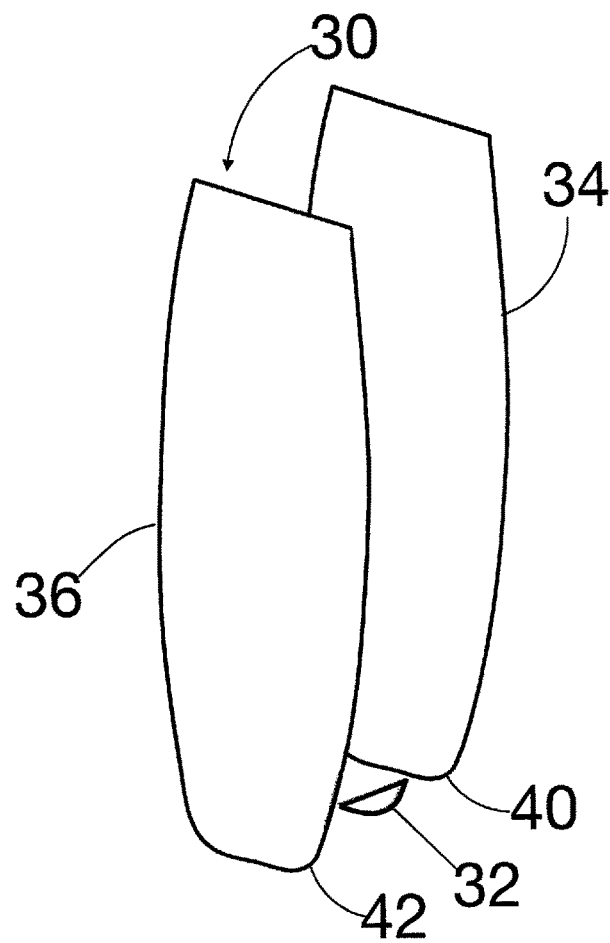
FIG. 6 is an exploded perspective view of a first body sheet, a second body sheet and a foot flap of a body compression sleepwear with a foot opening in accordance with the present invention.
Figure 7:
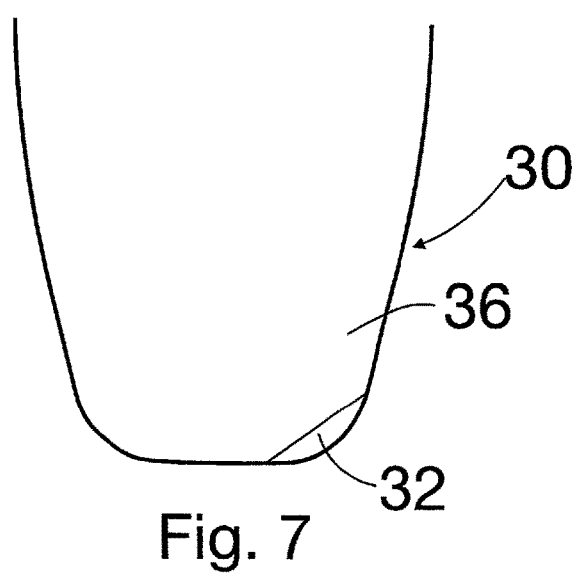
FIG. 7 is a front view of a bottom portion of a body compression sleepwear with a foot opening illustrating a foot flap in accordance with the present invention.

With reference to FIGS. 5-7, the body compression sleepwear with a foot opening preferably includes a body portion 30, the neck portion 12 and a foot flap 32. FIGS. 5-7 incorporate by reference FIGS. 1-4 in their entirety. The neck portion 12 may be eliminated. The body portion 30 includes a first body sheet 34 and a second body sheet 36. The first and second body sheets 34, 36 preferably include a slim oval shape, which are truncated on both ends with a straight edge. An outer perimeter of the first and second body sheets 34, 36 are sewn to each other with the exception of a top straight edge 35, 37 of the first and second body sheets 34, 36 to form a body pocket and bottom corner edges 40, 42 of the first and second body sheets 34, 36 are also not sewn to each other to form a foot opening. However, the foot opening could created at any location in a bottom of the body portion 30 with or without the foot flap 32.

Dashed lines on the first and second body sheets 34, 36 in FIG. 5 indicate the areas that are not sewn. The foot flap 32 is sewn to the bottom corner edge 40 of the first body sheet 34. The bottom corner edge 42 of the second body sheet 36 is inserted into the foot flap 32, but may be removed to allow a foot to be inserted through the foot opening. A bottom of the neck portion 12 is sewn to the top straight edge 35, 37. A length of the neck portion 12 is preferably about 10 percent of a length of the body portion 10. A width of the neck portion 12 is preferably about 70 percent of a width of the body portion 10. The material of the body portion 10 and the neck portion 12 is preferably fabricated from a combination Polyester and Lycra® fabric for stretch and memory. The size of the body compressive sleepwear with a foot opening is smaller than the user to exert compressive force on the outer surface of the body of the user.

Figure 8:
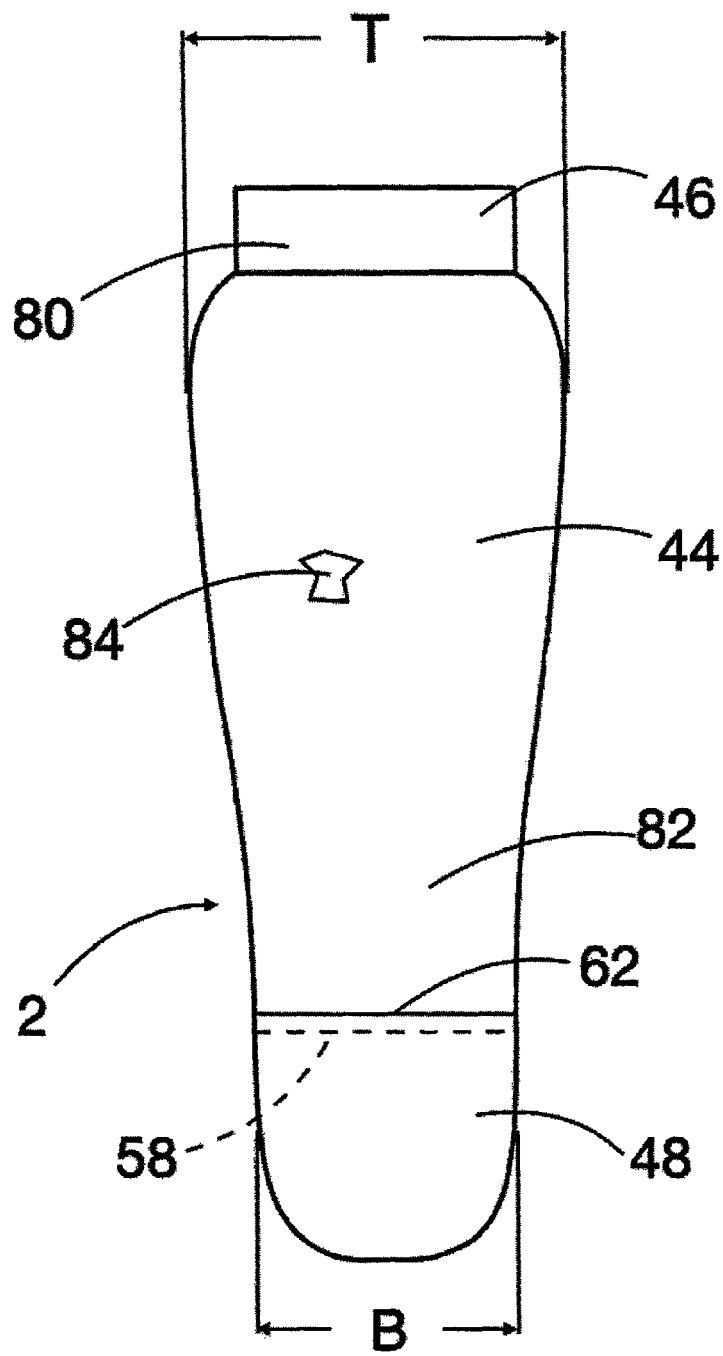
FIG. 8 is a front view of a body compression sleepwear with a leg opening in accordance with the present invention.
Figure 9:
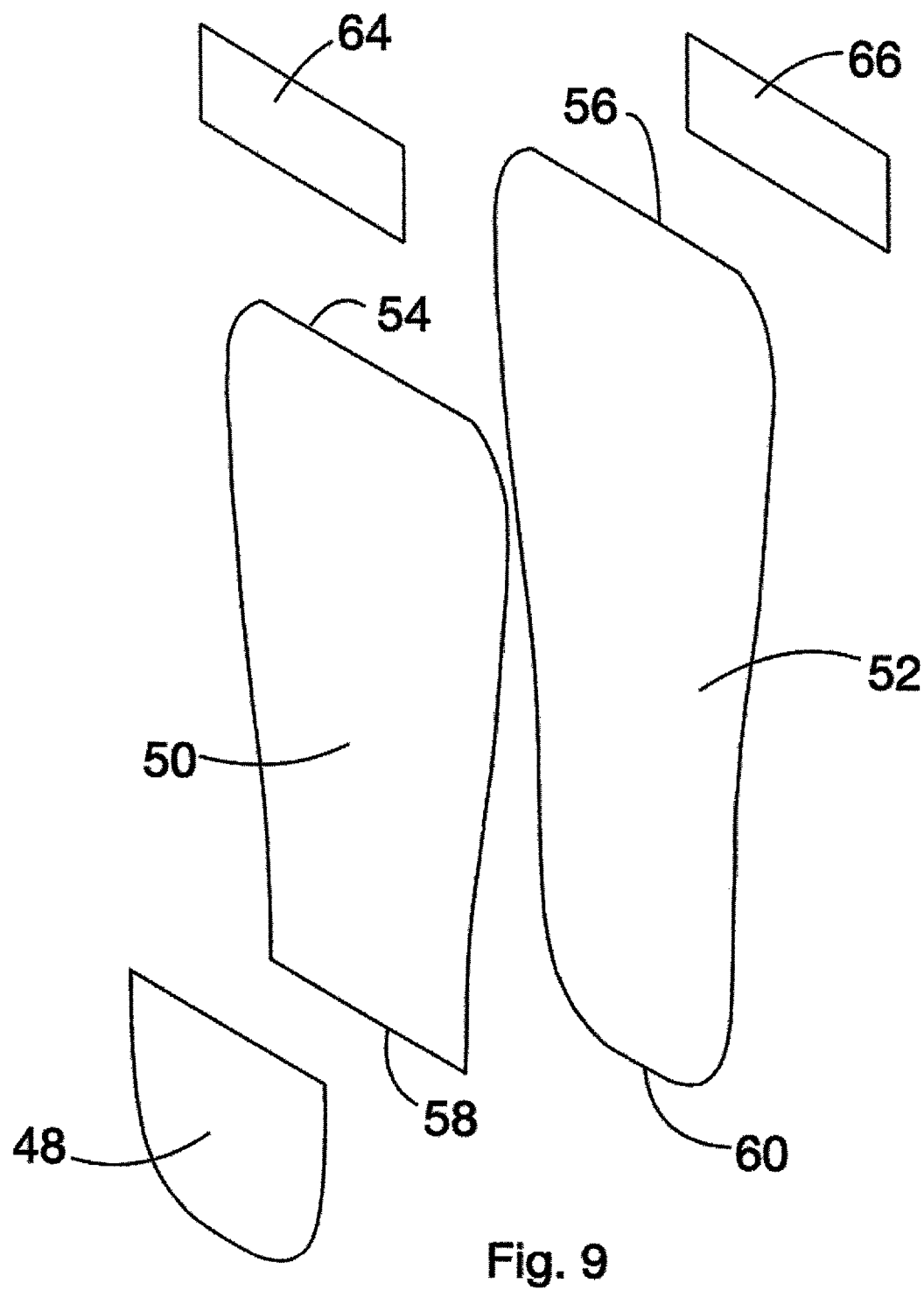
FIG. 9 is an exploded perspective view of a body compression sleepwear with a leg opening in accordance with the present invention.

With reference to FIGS. 8-9, the body compression sleepwear with a leg opening 2 preferably includes a body portion 44, a neck portion 46 and a leg cover 48. FIGS. 8-11 incorporate by reference FIGS. 1-7 in their entirety. The body portion 44 preferably includes a first body sheet 50 and a second body sheet 52. The first and second body sheets 50, 52 include a top width T which is greater than a bottom width B. A side of the first and second body sheets 50, 52 are tapered from the top width T to the bottom width B. The following range is given by way of example and not by way of limitation. The bottom width B is 60-80% of the top width T. The body compression sleepwear with a leg opening 2 preferably comes in different sizes for adults, children and babies. A top of the first and second body sheets 50, 52 preferably include a top straight edge 54, 56. A bottom of the first sheet 50 preferably includes a bottom straight edge 58. A bottom of the second sheet 52 preferably includes a U-shaped portion 60. A bottom of the first sheet 50 is truncated at a bottom, such that a top of the leg cover 48 overlaps the bottom straight edge 58. Outer sides of the first and second body sheets 50, 52 are attached to each other with sewing or like, such that a body opening is formed at a top and a leg opening is formed on a bottom thereof. A perimeter of the leg cover 48 is sewn to the U-shaped portion 60 of the second sheet 52 and a bottom portion of the first sheet 50 with exception of a top straight edge 62 of the leg cover 48.

Figure 10:
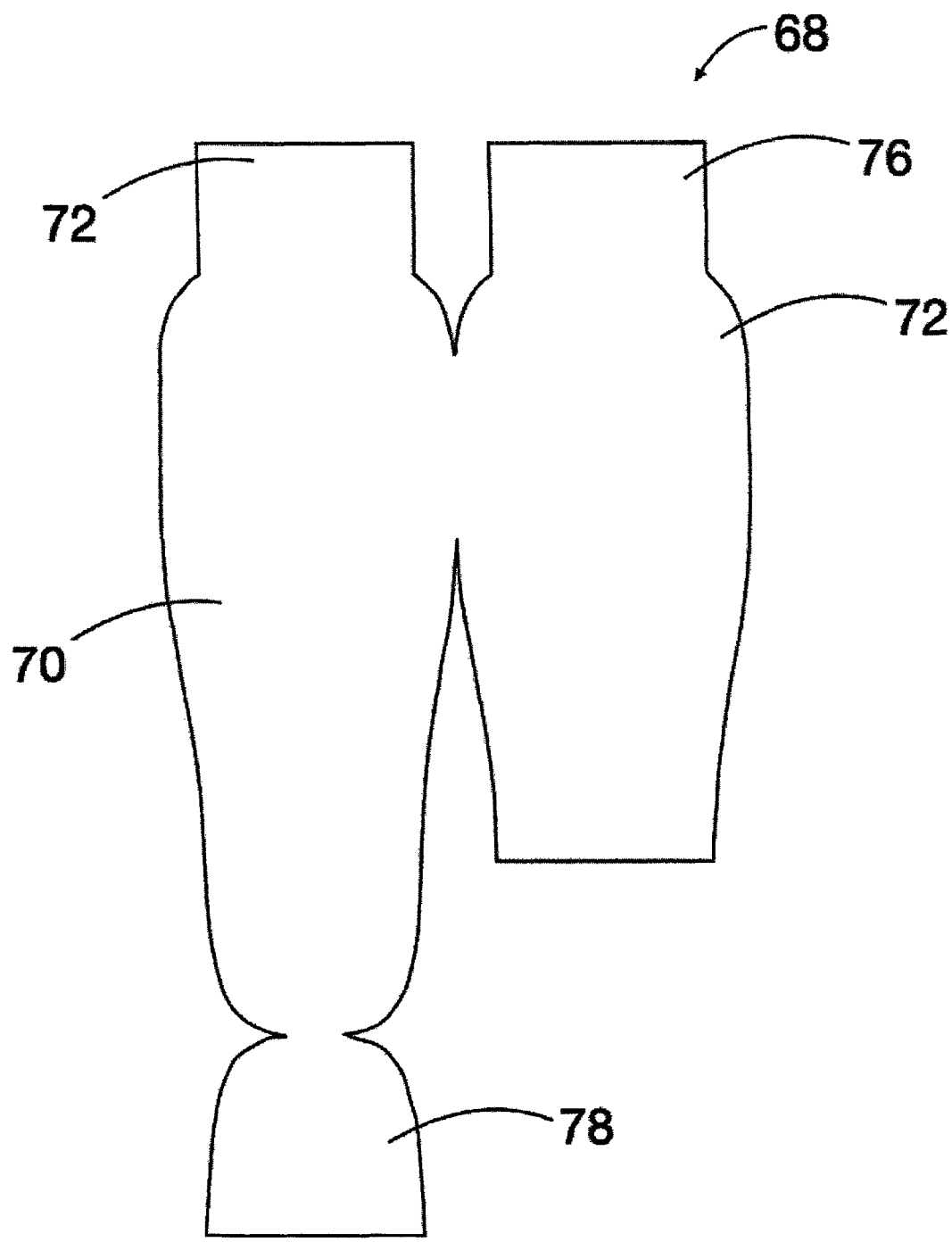
FIG. 10 is a front view of a single unsewn sheet which will create a body compression sleepwear with a leg opening in accordance with the present invention.

The neck portion 46 preferably includes a first neck sheet 64 and a second neck sheet 66. A bottom of the first neck sheet 64 is attached to the first straight edge 54 of the first body sheet 50. A bottom of the second neck sheet 66 is attached to the second straight edge 56. A length of the neck portion 46 is preferably about 10 percent of a length of the body portion 44. A width of the neck portion 46 is preferably about 75 percent of a width of the body portion 46, but other dimensions may also be used. Ends of the first and second neck 64, 66 sheets are sewn to each other to form a tube. However, the neck portion 46 could be eliminated. With reference to FIG. 10, the body compression sleepwear with a leg opening 2 may be fabricated from a single sheet 68. The single sheet 68 preferably includes a first body portion 70, a second body portion 72, a first neck portion 74, a second neck portion 76 and a leg cover 78. A second perimeter portion of the second body portion 72 extends from a first perimeter portion of the first body portion 70. A bottom cover perimeter portion of the leg cover 78 extends from a bottom body perimeter portion of the second body portion 72. The first neck portion 74 extends from a top of the first body portion 70. The second neck portion 76 extends from a top of the second body portion 72.

Figure 11:
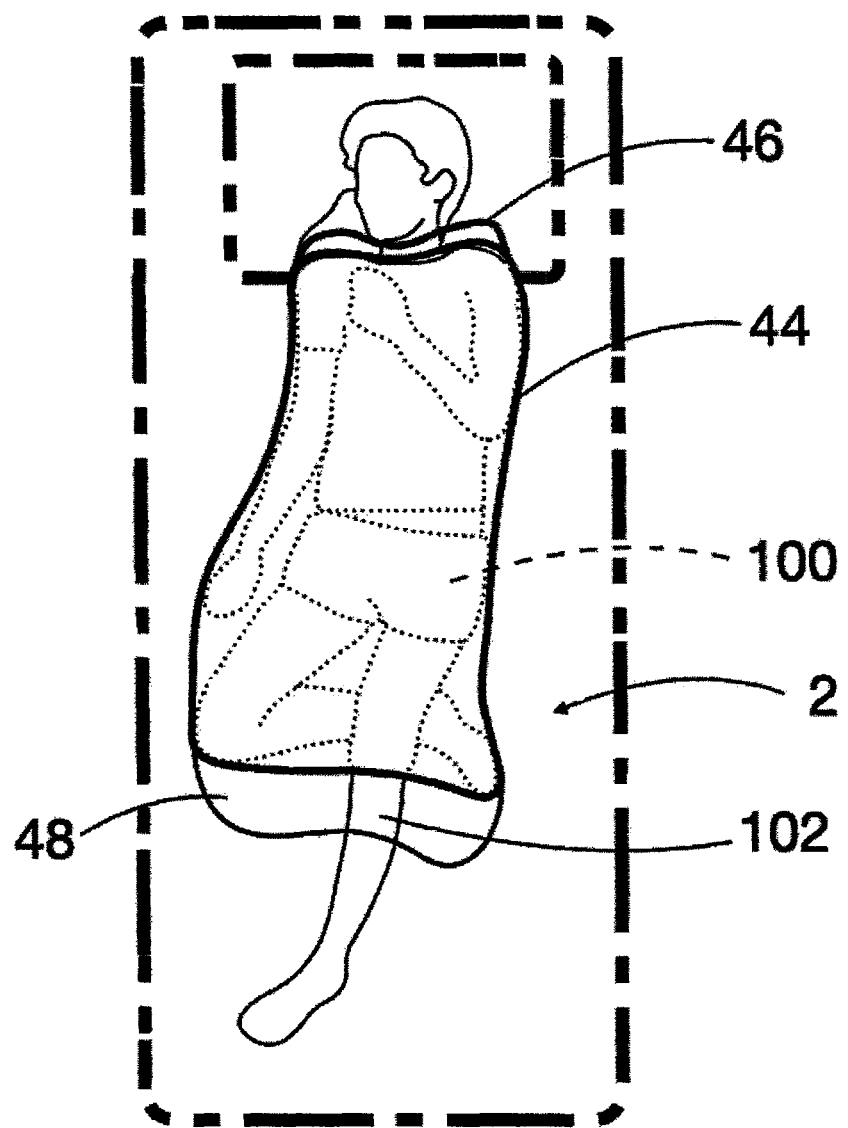
FIG. 11 is a top view of a user contained inside compression sleepwear with a leg opening in accordance with the present invention.

With reference to FIG. 8, the first body sheet 70 is attached to a perimeter of the second body sheet 72 to form a body portion 44. The body portion 44 includes a body entrance 80, a leg exit 82 and a body pocket 84. With reference to FIG. 11, a user 100 inserts their body through the body entrance 80. The body portion 44, the neck portion 46 and the leg cover 48 and the single sheet 68 are preferably fabricated from a blend of Polyester and Lycra® fabric for stretch and memory. With reference to FIG. 11, a user 100 is shown inside the body compression sleepwear with a leg opening 2 with one leg 102 extended through a gap between the leg cover 48, 78 and the second sheet 52, 72. However, both legs may be extended through the gap between the leg cover 48, 78. The body compression sleepwear with a leg opening 2 with both legs extending through the gap may be worn as an article of clothing, which has the advantage of compressing the body of the user during use. The leg cover 48, 78 may be attached to the second sheet 52, 72 gap with a zipper, snaps, hook and loop fasteners, or any other suitable attachment device. The body compression sleepwear with a leg opening 2 stretches to conform to the body of the person 100.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

I claim:

1. Body compression sleepwear with a leg opening comprising:
    a body portion including a body cavity, said body cavity is sized to receive a body of a user, said body portion includes a body entrance, a body pocket and a leg exit, wherein the user inserts their body through said body entrance, a truncated bottom is formed on a front portion of the body portion,
    a neck portion having an inner perimeter and a vertical height that extends upward from a top of said body entrance, said inner perimeter is equal to a perimeter of said body entrance; and
    a leg cover includes a bottom leg perimeter and a top leg edge, said top leg edge is not attached to said truncated bottom, said leg cover is attached to a perimeter portion of said body pocket, wherein the user is capable of inserting at least one leg through a gap between said truncated bottom and said top leg edge, said body portion and said leg cover are fabricated from a stretchable material with memory, a length and width of said body compression sleepwear is configured to provide compression of the user, said body compression sleepwear includes an unstretched configuration and a stretched configuration, a length and width of said body compression sleepwear is greater in said stretched configuration than in said unstretched configuration, wherein a length and width of said compressive sleepwear is configured to be smaller than a length and width of the user to exert compressive force on the outer surface of a body of the user.

2. The body compression sleepwear with a leg opening of claim 1 wherein:

a length of said neck portion is 10 percent of a length of said body portion.

3. The body compression sleepwear with a leg opening of claim 1 wherein:
a width of said neck portion is 75 percent of a width of said body portion.

4. The body compression sleepwear with a leg opening of claim 1 wherein:
said stretchable material is fabricated from a combination of polyester and spandex.

5. The body compression sleepwear with a leg opening of claim 1 wherein:
said stretchable material is composed of 89 percent polyester and about 11 percent spandex.

6. Body compression sleepwear with a leg opening comprising:
a body portion including a body cavity, said body cavity is sized to receive a body of a user, said body portion includes a body entrance, a body pocket and a leg exit, wherein the user inserts their body through said body entrance, a truncated bottom is formed on a front portion of the body portion, a top of said body portion is wider than a bottom of said body portion to form a tapered shape;
a neck portion having an inner perimeter and a vertical height that extends upward from a top of said body entrance, said inner perimeter is equal to a perimeter of said body entrance; and
a leg cover includes a bottom leg perimeter and a top leg edge, said top leg edge is not attached to said truncated bottom, said leg cover is attached to a perimeter portion of said body pocket, wherein the user is capable of inserting at least one leg through a gap between said truncated bottom and said top leg edge, said body portion and said leg cover are fabricated from a stretchable material with memory, a length and width of said body compression sleepwear is configured to provide compression of the user, said body compression sleepwear includes an unstretched configuration and a stretched configuration, a length and width of said body compression sleepwear is greater in said stretched configuration than in said unstretched configuration, wherein a length and width of said compressive sleepwear is configured to be smaller than a length and width of the user to exert compressive force on the outer surface of a body of the user.

7. The body compression sleepwear with a leg opening of claim 6 wherein:
a length of said neck portion is 10 percent of a length of said body portion.

8. The body compression sleepwear with a leg opening of claim 6 wherein:
a width of said neck portion is 75 percent of a width of said body portion.

9. The body compression sleepwear with a leg opening of claim 6 wherein:
said stretchable material is fabricated from a combination of polyester and spandex.

10. The body compression sleepwear with a leg opening of claim 6 wherein:
said stretchable material is composed of 89 percent polyester and about 11 percent spandex.

11. Body compression sleepwear with a leg opening comprising:
a body portion including a body cavity, said body cavity is sized to receive a body of a user, said body portion includes a body entrance top end and a closed bottom end, said body portion includes an upper portion and a lower portion;
a neck portion having an inner perimeter and a vertical height that extends upward from a top of said body entrance, said inner perimeter is equal to a perimeter of said body entrance; and
an opening in said lower portion extending across a width of a front side of said lower portion, wherein said opening has a top edge and a bottom edge, wherein the user is capable of inserting at least one leg through said opening to extend the at least one leg outside of the body portion, said body portion is fabricated from a stretchable material with memory, a length and width of said body portion is configured to provide compression of the user, said body portion includes an unstretched configuration and a stretched configuration, a length and width of said body portion is greater in said stretched configuration than in said unstretched configuration, wherein a length and width of said compressive sleepwear is configured to be smaller than a length and width of the user to exert compressive force on the outer surface of a body of the user.

12. The body compression sleepwear with a leg opening of claim 11, further comprising:
said body portion is tapered such that said lower portion is narrower than said upper portion.

13. The body compression sleepwear with a leg opening of claim 11 wherein:
a length of said neck portion is 10 percent of a length of said body portion.

14. The body compression sleepwear with a leg opening of claim 11 wherein:
a width of said neck portion is 75 percent of a width of said body portion.

15. The body compression sleepwear with a leg opening of claim 11 wherein:
said stretchable material is fabricated from a combination of polyester and spandex.

16. The body compression sleepwear with a leg opening of claim 11 wherein:
said stretchable material is composed of 89 percent polyester and about 11 percent spandex.

\* \* \* \* \*